United States Patent
Kranendonk

[11] Patent Number: 5,617,952
[45] Date of Patent: Apr. 8, 1997

[54] SUTURE NEEDLE PROTECTOR

[76] Inventor: Donald H. Kranendonk, 3812 Kingbird Ave., Wausau, Wis. 55401

[21] Appl. No.: 163,162

[22] Filed: Dec. 7, 1993

[51] Int. Cl.$^6$ .............. B65D 85/28; A61B 17/06
[52] U.S. Cl. .............. 206/380; 206/63.3; 206/818; 206/805
[58] Field of Search .............. 206/380, 383, 206/63.3, 818, 805, 38; 220/339

[56] References Cited

U.S. PATENT DOCUMENTS

| | | | |
|---|---|---|---|
| 1,066,129 | 7/1913 | Manasse | 206/38 X |
| 2,176,052 | 10/1939 | Beyer | 206/818 X |
| 2,893,548 | 7/1959 | Carver, Jr. et al. | 206/63.3 |
| 3,141,258 | 7/1964 | Mayer | 206/818 X |
| 3,301,393 | 1/1967 | Regan, Jr. et al. | |
| 3,376,973 | 4/1968 | Granowitz et al. | 206/63.3 |
| 3,661,248 | 5/1972 | Isen et al. | 206/5 A |
| 3,940,873 | 3/1976 | Lawless | 43/57.5 R |
| 3,944,069 | 3/1976 | Eldridge, Jr. | 206/350 |
| 4,013,109 | 3/1977 | Sandel | 206/350 X |
| 4,084,692 | 4/1978 | Bilweis | 206/63.3 X |
| 4,193,496 | 3/1980 | Barratt | 206/380 |
| 4,254,862 | 3/1981 | Barratt | 206/63.3 |
| 4,373,629 | 2/1983 | Ulin et al. | 206/850 |
| 4,596,329 | 6/1986 | Eldridge, Jr. | 206/63.3 X |
| 4,869,364 | 9/1989 | Bray | 206/232 |
| 4,969,893 | 11/1990 | Swor | 606/232 |
| 5,024,323 | 6/1981 | Bolton | 206/63.3 |
| 5,121,834 | 6/1992 | Tissembaum | 220/339 X |
| 5,148,916 | 9/1992 | Tillyer, Sr. | 206/38 X |

OTHER PUBLICATIONS

Photo copies of prototype suture needle protector, marked as Exhibit 1. Shown publicly by applicant at a trade show in the U.S. in Feb. 1992.

*Primary Examiner*—B. Dayoan
*Attorney, Agent, or Firm*—Foley & Lardner

[57] ABSTRACT

A suture needle protector for holding needles during surgical operations includes a cover attached to a base by a hinge to allow selective opening and closing of the cover with respect to the base. The suture needle is held within the protector temporarily, such as during tying off of a suture knot. A flexible elastic strap may be attached to the base to allow the protector to be mounted on the finger of the surgeon where the protector is conveniently available at a known location. A magnetic plate may be mounted within the base to help draw a surgical needle to the base and hold it in place when the cover is open. The cover is releasably held to the base by mating hook and lip structures on the cover and base to provide a snap connection. When the surgeon wishes to open the cover, pulling the cover from the base disengages the snap connectors. Because the protector can be mounted on the finger of the surgeon, when the needle is held within the closed protector with the suture extending from the protector the surgeon can use the protector during tying off to pull on the suture.

13 Claims, 3 Drawing Sheets

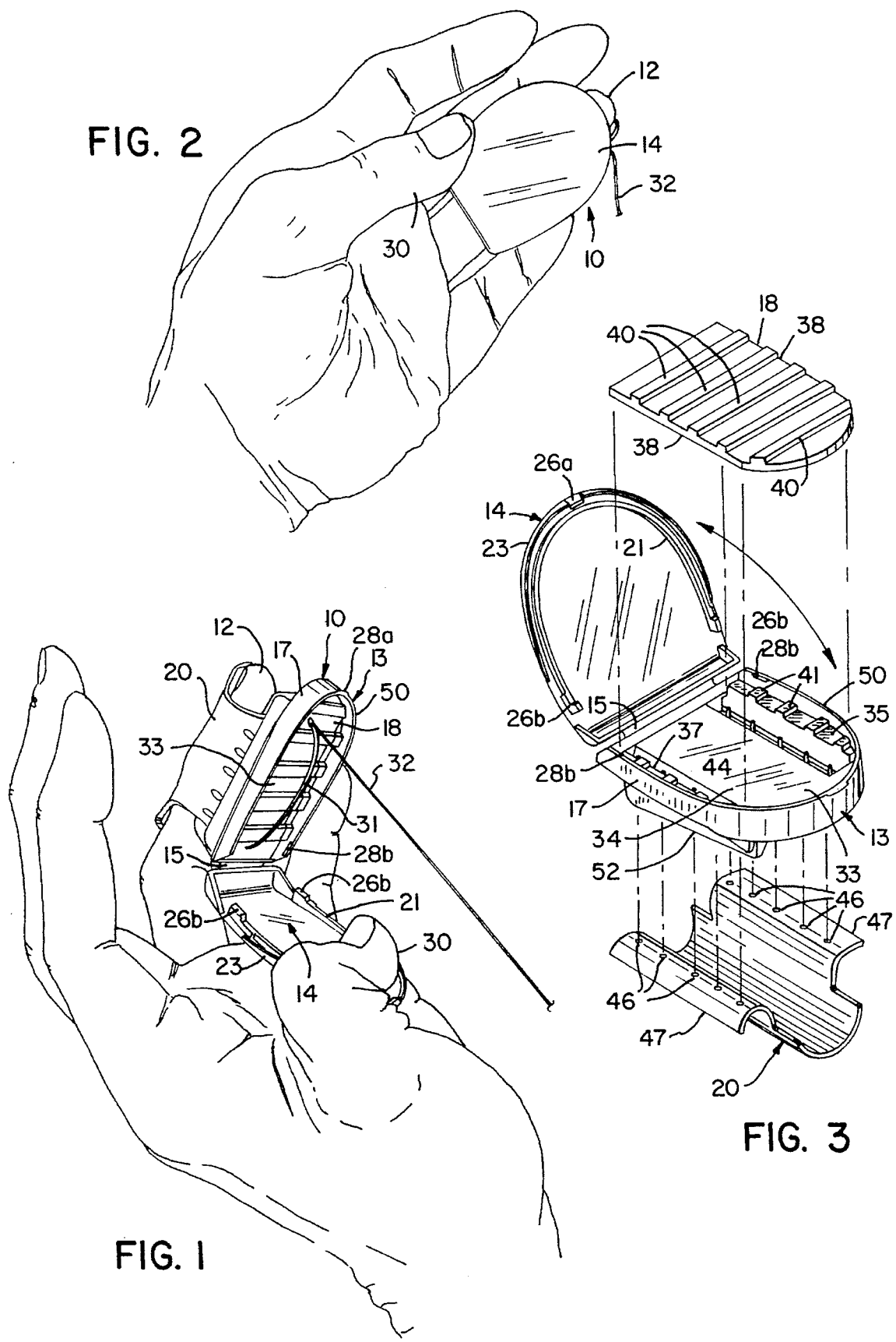

SUTURE NEEDLE PROTECTOR

FIELD OF THE INVENTION

The present invention pertains generally to the field of surgical devices and particularly to apparatus for protecting a surgeon or other medical personnel from accidental suture needle puncture wounds during the course of an operation or other medical procedure.

BACKGROUND OF THE INVENTION

Many common medical procedures involve closing tissue by the use of sutures. A suture is a strand or fiber which holds previously opened tissue shut after the suture is driven through the tissue by the use of a suture needle. The suture needle is a needle-like instrument with an extremely sharp point at one end and with the suture being attached to its other end. Suture needles vary in size and shape, and the choice of a particular size or shape of suture needle is dictated by the type of medical procedure to be performed. One common form of suture needle has an arcuate configuration. Using the suture needle in combination with a suture, medical personnel close tissue by sewing it together in much the same manner that two pieces of cloth are sewn together.

However, the use of a suture needle on living tissue obviously requires precautions which need not be followed when sewing non-living material. While working on living tissue, the suture and suture needle must at all times remain sterile to minimize the risk of infection to the patient. Since many common medical procedures require the surgeon to use a number of different tools, thereby requiring the surgeon to repeatedly put down one tool and pick up another, the surgeon must be careful to keep the suture needle in a sterile area as it is exchanged for another tool. Further, the suture needle, as well as other tools, must be readily at hand for the surgeon's instant use during the operation. This is not simply a matter of convenience, because the patient's safety may depend on a specific tool being quickly available if it should be needed. Therefore, the suture needle (and other instruments) must be placed on a convenient sterile surface during an operation so that they may be readily accessed by the surgeon, while maintaining the sterility of the operating area.

In addition, the surgeon must take care that he or she does not accidentally injure himself or herself with a suture needle that has been used to suture tissue. Since any patient could potentially carry a disease such as the human immunodeficiency virus (HIV), even the smallest puncture wound can be life-threatening. The surgeon, who works with gloved hands to decrease the possibility of contamination, may have difficulty picking up the needle from a flat surface due to interference from the gloves and a corresponding partial loss of tactile sensation in the fingers. If the surgeon must expend effort by pushing the needle to align it into a position where it may be easily picked up, the opportunity for accidental puncture is increased. The chance of puncture is also increased if the surgeon must put down and pick up a suture needle (with a suture attached) several times during the course of an operation. A surgeon must therefore pay close attention to the handling of suture needles as well as to the patient undergoing the operation.

In the environment in which many medical operations take place, these requirements are inconvenient. During an operation, the surgeon must devote the bulk of his or her attention to the patient. The surgeon cannot afford to spend a great amount of time during the course of an operation repositioning the suture needle so that it may be easily found and so that it is certain to remain in a sterile environment. Further, the need for the surgeon's full attention to be focused on the patient fosters an environment in which the surgeon can become inattentive as to the handling of tools, thus increasing the risk of self-injury. Suture needles present an especially high risk of injury due to their small size and extreme sharpness. In view of these requirements, it would be helpful if a surgeon had a readily accessible surface or receptacle in which a suture needle could be placed which would shield the surgeon from accidental puncture while at the same time facilitating the surgeon's access to the needle. Examples of surgical needle containers are shown in U.S. Pat. Nos. 4,193,496, 4,373,629, 4,596,329, 4,969,893 and 5,024,323. Such devices generally have not been convenient to use, or are not intended for temporary placement of a suture needle during an operation, and typically do not allow convenient reloading of the suture needle for the next stich. Devices intended to be used repeatedly during an operation often are inconvenient to use because they must be set to the side of the surgical area and may slip off the surgical drapes or be difficult to locate quickly when they are needed.

SUMMARY OF THE INVENTION

The surgical needle protector of the present invention has a base and a cover which are attached by a hinge. When the cover is closed on the base, a suture needle resting within the protector is enclosed between the base and cover so that it will not injure the user, and when the cover is opened from the base and rotated about the hinge, the user can reach between the base and cover to deposit or access the suture needle. The base includes an inner base surface from which a base wall preferably rises, and the cover includes an inner cover surface from which at least one cover rib preferably rises. The inner base surface is substantially surrounded by the base wall, and the portion of the inner base surface that is so surrounded has a size such that a suture needle may fit upon it. When the holder is closed, the inner base surface and the inner cover surface lie spaced from and facing each other, and a suture needle resting on the inner base surface will be surrounded by the inner base surface, the base wall, and the inner cover surface, with the inner cover surface separated from the inner base surface by the height of the base wall. The cover rib is oriented along the inner cover surface so that when the base and cover rest in the closed state, the cover rib lays closely adjacent but is spaced from the base wall. If one cover rib is used, it may either surround the base wall and form the outermost exterior wall of the holder when the protector is closed, or it may be surrounded by the base wall. If two cover ribs are used, the two ribs will be positioned on opposite sides of the base wall when the holder is closed. The close spaced relation of the cover rib(s) and the base wall prevents a suture needle from slipping between the cover rib(s) and base wall and accidentally falling out of the protector. An inflexible suture needle cannot fit between the base wall, the inner cover surface, and the cover rib(s). When the cover is opened from the base, the inner base surface is exposed so that a suture needle may be deposited upon or removed from the inner base surface.

The protector may include mounting structure, preferably a strap of elastic attached to the base, for mounting the protector to an appendage of the user, such as to a finger or wrist. The user may therefore mount the protector on a finger or wrist so that the location of the protector is always known and the protector is always readily accessible. The base may also include a plate made of a magnetic material or a soft, puncturable material, on the inner base surface so that the suture needle may be stuck onto or into the plate to minimize the possibility of the suture needle accidentally falling out of the protector when it is open.

The suture needle protector of the present invention conveniently holds and protects the surgical needle during the course of an operation while avoiding several of the problems found in prior surgical needle containers. When closed, the protector completely encloses the suture needle and thereby protects personnel from accidental puncture. The protector may be reopened and reclosed repeatedly so that the suture needle may be deposited within or removed as many time as desired. The protector is preferably equipped with an adjustable mounting strap on its base so that it may be mounted on a surgeon's finger so that the suture needle will at all times be in a known position of ready accessibility. For example, a right-handed surgeon could mount the protector on the ring finger of the left hand so that it faces the thumb of the same hand. The thumb may then be used to disengage the cover of the protector, and the right hand may be used to pick up the suture needle for use. Because the protector is never further away than the surgeon's hand and the surgeon knows at all times where it is, the suture needle is always at a position where the surgeon may readily access it. Such placement of the protector also facilitates its use in tying off sutures, the action of which may be obtained by withdrawing the hand upon which it is mounted away from the wound. The interior surface of the protector is preferably contoured so that a surgeon may easily pick up the suture needle from the surface without needing to push the needle into a position where it is more easily grasped. The inner base surface of the protector may include a magnetic plate containing spaced ribs that allow the suture needle to be gripped, as by a needle holder, regardless of the orientation of the suture needle on the plate. The base and cover of the protector may be snapped together after the suture needle is placed within, and afterwards the protector can only be opened when an external force is applied by the user. Even when the protector is opened, the magnetic plate may be utilzed to hold the suture needle and restrain it from falling out.

Further objects, features, and advantages of the invention will be apparent from the following detailed description when taken in conjunction with the accompanying drawings.

BRIEF DESCRIPTION OF THE DRAWINGS

In the drawings:

FIG. 1 is a perspective view of the suture needle protector of the invention mounted on a finger of a user in its open state.

FIG. 2 shows a perspective view of the protector mounted on the finger of a user in its closed state.

FIG. 3 shows an exploded perspective view of the protector.

DETAILED DESCRIPTION OF THE INVENTION

Figure 6:
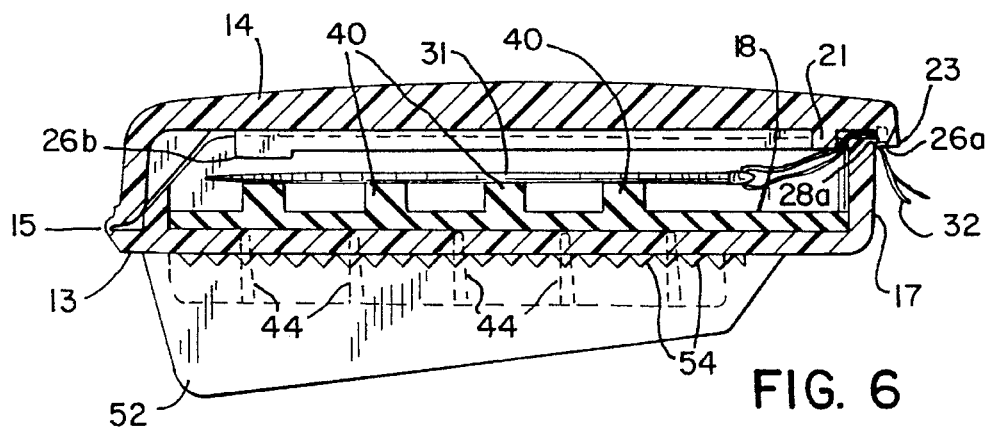
FIG. 6 shows a cross-sectional view of the protector taken along the line 6—6 in FIG. 4.

With reference to the drawings, the suture needle protector of the invention is shown generally at 10 mounted in its open position on the ring finger 12 of a surgeon's hand. The protector is intended to be mounted on the user's non-dominant hand, i.e. the left-hand for a right-handed user, so that the dominant hand is free. The protector 10 includes a base 13 and a cover 14 which may be moved about a hinge 15. The base 13 includes a base wall 17, which extends about the periphery of the base 13, a permanent magnetic plate 18 upon which the suture needle can be placed, and a mounting strap 20 for mounting the base 13 to the user. The cover 14 includes an inner cover rib 21 and an outer cover rib 23, which both extend from the inner surface 24 of the cover top wall 25 spaced from one another and may be generally (although not necessarily) parallel. One or more snapping hooks 26 extend from the cover, each of which can engage a lip 28 on the base 13 to hold the protector in its closed position. As best shown in FIG. 6, a backwall 27 of the cover extends downwardly from the top wall 25 to the hinge 15. The protector is shown in FIG. 1 in its open state, with the cover 14 being held open by the user's thumb 30 so that a needle holder or the fingers on the user's other hand may reach within the protector to pick up or deposit a suture needle on the magnetic plate 18. The cover 14 may also be moved about the hinge 15 into the closed state, as shown in FIG. 2, wherein the cover 14 engages the base wall 17. Because a suture needle 31 within the closed protector is completely enclosed by the base 13, the base wall 17, and the cover 14, the user is shielded from accidental puncture wounds. In the closed state, a flexible suture 32 can extend out of the protector, as illustrated in FIG. 2.

FIG. 3 shows an exploded view of the protector 10. An inner base surface 33 includes a central section 34 and two side shoulders 35 on opposite sides of the central section 34. The base wall extends from and at least partially surrounds the inner base. Two slots 37 extend on opposite sides of the central section 34 between the central section and the side shoulders 35. The magnetic plate 18 may be inserted within the protector so that it rests on the central base surface section 34 with its opposite edges 38 in close proximity to the side shoulders 35. When so placed, the surface of the magnetic plate 18 forms part of the inner base surface 33. The purpose of the magnetic plate 18 is to restrain the suture needle 31, which is generally ferromagnetic, from easily falling out of the protector when the protector is in its open position and to restrain the needle from moving around during regrasping for its next use. An adhesive may be used to affix the magnetic plate 18 to the central base surface 34, or, alternatively, the magnetic plate 18 may be sized to fit tightly between the two side shoulders 35. Of course, the magnetic plate may be eliminated, if desired. In such a case, the surface of the base would preferably, although not necessarily, have ribs formed therein as discussed below.

As illustrated in FIGS. 1 and 3, the magnetic plate 18 preferably includes a number of ribs 40 which align with shoulder ribs 41 on the side shoulders 35 to form a series of continuous ribs on the inner base surface when the magnetic plate 18 is placed within the base 13. The ribs 40 are preferably provided so that the user can reach under the suture needle 31, as with a needle holder, to more easily pick up the needle.

FIG. 3 illustrates the mounting strap 70 in greater detail and spaced away from the base. The mounting strap 20 is used to mount the protector to the user, as to a finger or thumb, or if the strap is made long enough, to the user's hand or wrist. A preferred means of attaching the strap 20 to the base 13 is illustrated with respect to FIG. 3. As shown in FIG. 3, associated with each of the slots 37 are several mounting prongs 44 which extend and taper upwardly within each slot 37. The mounting strap 20 includes several spaced holes 46 in lines adjacent to opposite edges 47 of the mounting strap 20. To attach the strap 20 to the base 13, each edge 47 of the strap is extended through openings 48 (shown in FIG. 5) in the base, and each mounting prong 44 is then inserted into one of the holes 46 so that the mounting strap is retained by the prongs 44. After the mounting strap 20 is attached to the base in this manner, the magnetic plate 18 can be installed on the central base surface 34, where it covers the slots 37 and forms a continuous ribbed surface in combination with the side shoulders 35.

The mounting strap 20 may be made of any flexible material, the preferred material being rubber because of its elasticity and its slippage-preventing frictional properties. Inflexible bands or straps, which may be permanently affixed to the base 13 or another part of the holder, are alternate means of mounting the holder to the user, but are not preferred because they do not offer the versatility of a removable and flexible strap. The straps 20 may be made in an assortment of sizes and shapes to allow the protector 10 to be mounted on different appendages of the user and different sites on these appendages. While FIGS. 1 and 2 show the protector mounted on the user's ring finger facing the interior of the user's hand, the protector may be mounted on the user's hand (e.g., situated in the palm) or on the wrist. The mounting location shown in FIGS. 1 and 2 is generally the most convenient because it allows the user to open and close the protector by working the cover 14 with the thumb. Although the protector of the present invention is inexpensive and readily disposable after use, if desired, the mounting strap 20 may be disposed of after an operation and replaced with a new mounting strap after the rest of the protector is sterilized, or the entire protector including mounting strap may be re-sterilized if made of the proper material.

Figure 4:
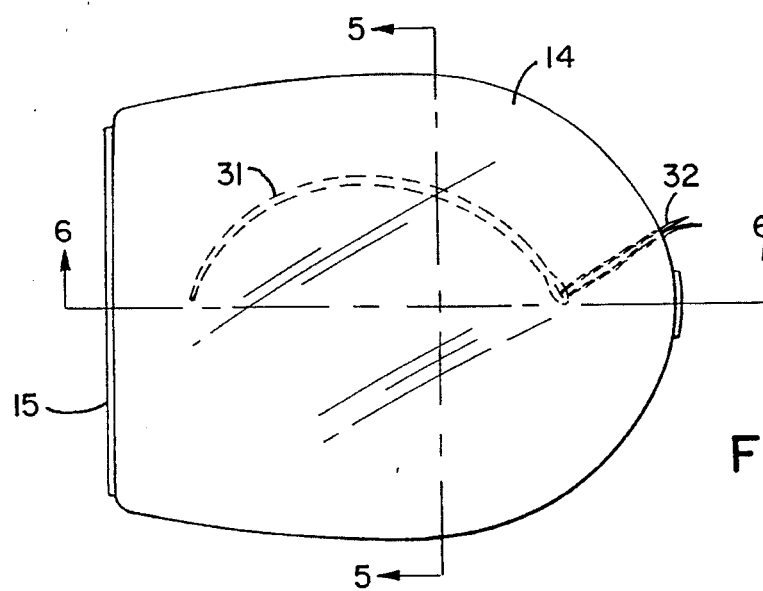
FIG. 4 shows a plan view of the protector in its closed state.
Figure 7:
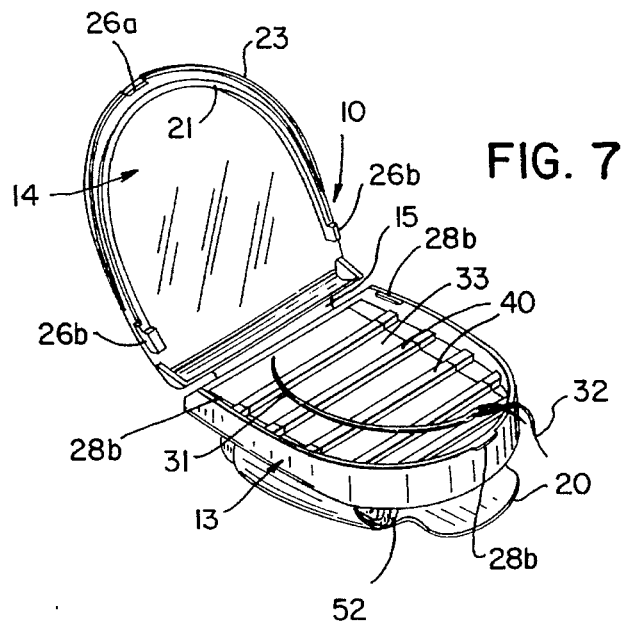
FIG. 7 shows a perspective view of the protector in its open state with a suture needle resting within.

FIG. 4 illustrates the position of the suture needle 31 (in phantom) within the closed protector. As illustrated in the cross-sectional views of FIGS. 5 and 6, when the protector 10 is closed, the suture needle 31 is completely surrounded by the base 13 and the cover 14. The cover 14 rests on the base wall 17 with the inner cover surface engaging the base wall top edge 50, and the cover 14 is firmly held atop the base 13 by attachment features discussed further below. The base wall 17 is situated between the inner cover rib 21 and the outer cover rib 23. The suture needle 31 sits atop the support ribs 40 on the magnetic plate 18 with the suture 32 extending from its end, as illustrated in FIG. 6. The suture 32 extends from the suture needle 30 under the inner cover rib 21, over the base wall top edge 50, and then under the outer cover rib 23 to the exterior of the protector (and to the patient). While a flexible suture can follow this path and can be pulled out, an inflexible suture needle cannot, and therefore the suture needle cannot easily be pulled out of the protector 10 if a pulling force is exerted on the suture. The only way the needle 31 can be pulled out of the closed protector is if enough force is applied on the suture and the needle to pull the cover open. Because the cover is firmly attached to the base, this is unlikely.

Further, when the cover 14 is held against the base 13 by the user (e.g., by applying pressure with the thumb) the cover will not open and the protector can be used to exert draw on the suture 32 during tying off.

Figure 5:
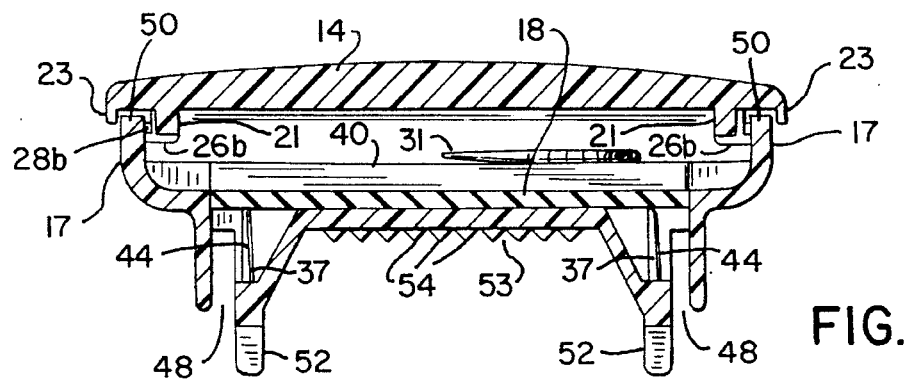
FIG. 5 shows a cross-sectional view of the protector taken along the line 5—5 of FIG. 4.

The preferred structure for releasably holding the cover closed onto the base is best illustrated in FIGS. 5–8. Such attachment of the cover 14 to the base 13 is necessary so that a tug on the suture of an enclosed suture needle will not cause the cover 14 to open. A first hook 26a on the forwardmost portion of the outer cover rib 23 engages a first lip 28a on the forwardmost portion of the base wall outer face when the protector is in the closed state and prevents the cover 14 from popping open when the suture is pulled. Two rear hook and lip combinations 26b and 28b are shown in FIGS. 5 and 6 in the engaged position when the protector is in the closed state, and in FIGS. 1, 7 and 8 when the protector is open. The rear hooks 26b are located at the back ends of the inner cover rib 21 where they engage rear lips 28b on the base wall 17 inner face when the cover 14 is pushed into the closed position. The hook 26b and lip 28b combinations have dimensions such that they will engage before the forward hook 26a and lip 28a as the cover is closed, and will disengage after the hook 26a and lip 28a as the cover is opened. The multiple connections between the cover and the base provided by the engaged hooks and lips helps ensure that the cover will remain tightly closed to the base so that the suture needle cannot be inadvertently pulled out.

If desired, other attachment structures may be used in place of the hook and lip combinations. Any of the commonly used mechanisms for locking shut the opposable halves of a container may be used. For example, a rodlike protrusion may extend from the base wall 17 with an aperture provided on the inner cover surface into which the rod may extend when the protector is closed. As a further example, a "U"-shaped leaf spring (not shown) could be slid over the base 13 and cover 14, with the hinge 15 at the vertex of the spring. The spring would tend to force the protector into the closed position, and the protector could be opened by lifting the cover 14 to access a suture needle within the protector, with the spring automatically closing the cover after the needle has been removed (or, conversely, inserted).

Figure 8:
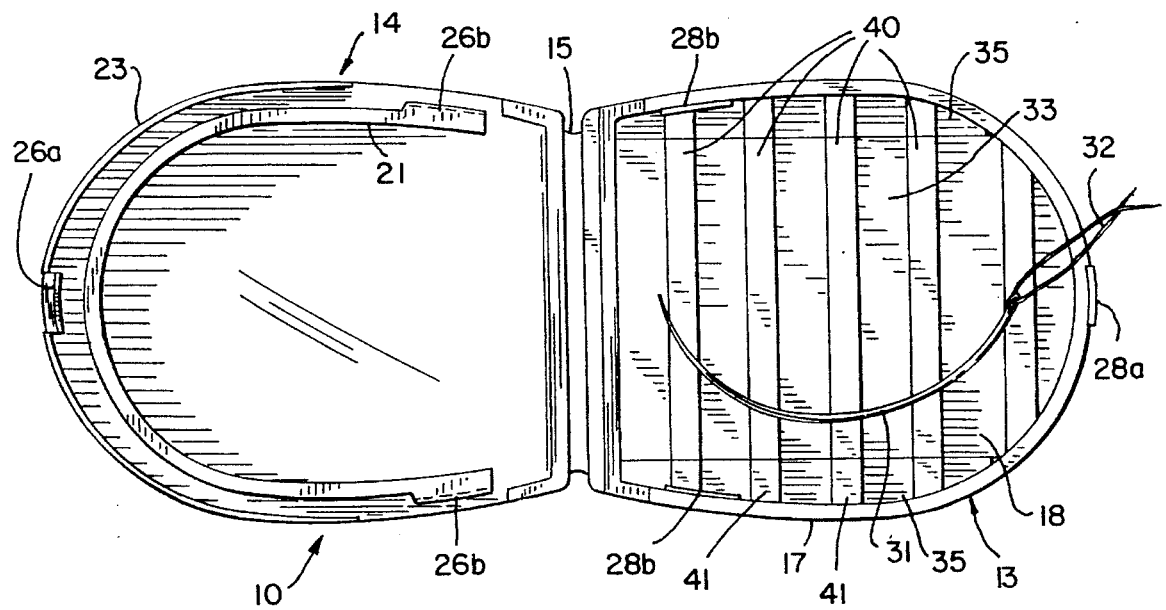
FIG. 8 shows a plan view of the protector fully opened.

With reference to FIG. 8, it is seen that the needle ribs 40 should preferably be spaced far enough apart so that the needle may easily be picked up from the magnetic plate, but are closely spaced enough so that the needle will not fall between the needle ribs. A needle rib width of about 0.09 inch, a rib height of about 0.06 inch, and a rib spacing of about 0.18 inch are typical for use with typical curved suture needles. However, the ribs may be wider, e.g., equal in width to the rib spacing, to increase the magnetic pull of the plate on the suture. To accomodate smaller needles, the ribs closest to the front of the protector may be narrower and more closely spaced.

The magnetic plate 18 holds the suture needle to the plate to prevent the suture needle from accidentally falling out of the protector. This plate may be formed of commercially available rubber or plastic material having permanent magnetic material therein. An exemplary material is ferrite in a plastic binder, and suitable magnetic material is available from Mag Tech (e.g., 0.7 MGoe). Other means of holding the needle onto the inner base surface may also be used. For instance, a soft plate made of foam rubber or felt could be affixed to the central base surface 34 so that the suture needle can be inserted within the plate, thereby fixing the suture needle until the user pulls it out.

The outer lower surface of the base 13 preferably includes two finger flanges 52 on either side of a central surface 53 which includes a pattern of protrusions 54 which help prevent slippage when the protector is mounted on a user's finger. When the protector is mounted on the user's finger, the finger is inserted between the finger flanges 52 and is held to the non-slip surface 53 by the mounting strap 20. The protrusions 54 on the surface 53 helps to prevent the protector from slipping across the user's finger as the user's non-dominant hand is used. The finger flanges 52 prevent lateral slippage of the holder on the user's finger. The finger flanges 52 could be eliminated or repositioned if the protector is intended to be affixed to an appendage of the user rather than a finger.

As best illustrated in FIG. 1, the cover back wall 27 which extends downwardly from the cover top wall 25 (e.g., about 3/16 inch) is positioned to engage the finger 12, or other appendage of the user on which the protector is mounted, as the cover is drawn open. This engagement tends to restrain the cover from being opened farther than about 90° with respect to the base-the position illustrated in FIG. 1. This is sufficient to allow full access to the inside surface of the base but helps to prevent overflexing of the integral hinge 15 which might occur if the cover were repeatedly opened and drawn to a flat position generally parallel to the base. Excessive flexing of an integral plastic hinge can lead to fatigue failure of the hinge.

The protector is preferably made of a sterilizable material such as polypropylene, styrene, or other types of plastics. A material that has been found suitable is clear styrene-butadiene copolymer KRO-3 K-resin available from Phillips Plastics division of Phillips Petroleum Co. The base 13, cover 14, and hinge 15 may preferably be a unitary structure formed by an injection molding process. As best shown in FIG. 6, the hinge 15 may be a "living hinge", formed of plastic integrally with the base and cover, which is sufficiently thin to be flexible. When using the foregoing styrene-butadiene copolymer, a satisfactory hinge 15 may be formed of a thinner section about 0.05 inch wide and about 0.016 inch thick, and thicker or thinner sections may be used depending on the desired stiffness of the hinge. The cover and base may also be formed separately and then assembled to one another using any available hinge structure. The mounting strap 20 may be made of various resilient materials, for example, surgical rubber. The relatively low material and production costs of the protector allows it to be disposed of after a single use.

The protector could, if desired, be altered in shape, size, and mounting location to accommodate other surgical implements as well as (or instead of) suture needles. The protector may also be used without the mounting strap 20, for example, by simply resting the protector on the surgical drapes adjacent to the patient. Further, if desired, the protector can be equipped to be held to the surgical drapes, or to the surgeon's finger or hand, as by Velcro™ type fasteners, clips, snaps, pins, etc.

It is understood that the invention is not confined to the particular embodiments described herein as illustrative, but embraces all such modified forms thereof as come within the scope of the following claims.

What is claimed is:

1. A suture needle protector for holding a suture needle during a surgical operation, comprising:

(a) a base having an inner base surface on which a suture needle can be placed;

(b) a cover sized to close over the base to hold a suture needle on the inner base surface surrounded by the base and the cover;

(c) a hinge hingedly attaching the cover to the base so that the cover can be moved from a closed position in which the cover and base enclose a suture needle to an opened position in which a suture needle can be placed in or removed from the area of the inner base surface;

(d) mounting means for mounting the base to a finger of a user; and (e) means for releasably holding the cover closed onto the base, wherein the base includes a base wall extending from and at least partially around the inner base surface, and wherein the means for releasably holding the cover onto the base comprises at least one lip formed on the base wall and at least one hook extending from the cover which is positioned to snap over and engage the lip on the base wall when the cover is moved to its closed position, and wherein one of said at least one lip is formed on the forwardmost portion of the base wall and a corresponding one of said at least one hook is formed on a corresponding forwardmost portion of the cover to engage the forwardmost lip on the base wall, and further including lips extending from the base wall at positions near the hinge and hooks extending from the cover at positions near the hinge to engage the lips on the base wall near the hinge as the cover is moved to its closed position.

2. A suture needle protector for holding a suture needle during a surgical operation, comprising:

(a) a base having an inner base surface on which a suture needle can be placed;

(b) a cover sized to close over the base to hold a suture needle on the inner base surface surrounded by the base and the cover;.

(c) a hinge hingedly attaching the cover to the base so that the cover can be moved from a closed position in which the cover and base enclose a suture needle to an opened position in which a suture needle can be placed in or removed from the area of the inner base surface; and (d) mounting means for mounting the base to a finger of a user, wherein the mounting means comprises a strap of flexible material, wherein the base includes strap slots extending through the base in spaced relation about a central outer base surface, mounting pins extending adjacent the strap slots, and holes formed in the mounting strap at positions near two edges of the strap such that the mounting pins extend through the holes in the strap to hold the strap to the base.

3. A suture needle protector for holding a suture needle during a surgical operation, comprising:

(a) base having an inner base surface on which a suture needle can be placed;

(b) a cover sized to close over the base to hold a suture needle on the inner base surface surrounded by the base and the cover;

(c) a hinge hingedly attaching the cover to the base so that the cover can be moved from a closed position in which the cover and base enclose a suture needle to an opened position in which a suture needle can be placed in or removed from the area of the inner base surface and (d) mounting means for mounting the base to a finger of a user, wherein the mounting means comprises a flexible and resilient strap attached to the base at two ends of the strap to define a region, through which a finger of the user may be inserted, between a bottom surface of the base and the strap to hold the protector on the finger of the user, and further including parallel finger flanges extending downwardly from the bottom surface of the base with the strap extending around the finger flanges so that the finger flanges help prevent the base from sliding off the finger of a user.

4. The protector of claim 3 further including a pattern of protrusions extending from the bottom base surface at a position to be engaged by the finger of the user to help prevent the protector from slipping off the finger of the user.

5. A suture needle protector for holding a suture needle during a surgical operation, comprising:

(a) a base having an inner base surface on which a suture needle can be placed and a base wall extending from and at least partially surrounding the inner base surface;

(b) a cover sized to close over the base to hold a suture needle on the inner base surface surrounded by the base and the cover, the cover having an inner cover rib which extends from an inner cover surface and which is positioned such that it extends substantially parallel to and spaced from the base wall when the cover is closed onto the base such that a suture needle resting on the inner base surface is substantially surrounded by the inner cover rib, and an outer cover rib extending from the inner cover surface substantially parallel to and spaced away from the inner cover rib by a distance such that the base wall is situated between and spaced away from the inner cover rib and the outer cover rib when the cover is closed onto the base; and (c) a hinge hingedly attaching the cover to the base so that the cover can be moved from a closed position in which the cover and base enclose a suture needle to an opened position in which a suture needle can be placed in or removed from the area of the inner base surface.

6. The protector of claim 5 including a strap of flexible material having ends attached to the base so that a user can insert a finger between the base and the strap to hold the protector on the finger of the user.

7. The protector of claim 6 wherein the strap is formed of a thin strip of resilient rubber.

8. The protector of claim 5 including means for releasably holding the cover closed onto the base.

9. The protector of claim 8 wherein the means for releasably holding the cover onto the base comprises at least one lip formed on the base wall and at least one hook extending from the cover which is positioned to snap over and engage the lip on the base wall when the cover is moved to its closed position.

10. A suture needle protector for holding a suture needle during a surgical operation, comprising:

(a) a base having an inner base surface on which a suture needle can be placed and a base wall extending from and at least partially surrounding the inner base surface;

(b) a cover sized to close over the base to hold a suture needle on the inner base surface surrounded by the base and the cover, the cover having an inner cover rib which extends from an inner cover surface and which is positioned such that it extends substantially parallel to and spaced from the base wall when the cover is closed onto the base such that a suture needle resting on the inner base surface is substantially surrounded by the inner cover rib, and an outer cover rib extending from the inner cover surface substantially parallel to and spaced away from the inner cover rib by a distance such that the base wall is situated between the inner cover rib and the outer cover rib when the cover is closed onto the base;

(c) a hinge hingedly attaching the cover to the base so that the cover can be moved from a closed position in which the cover and base enclose a suture needle to an opened position in which a suture needle can be placed in or removed from the area of the inner base surface; and (d) means for releasably holding the cover closed onto the base, comprising at least one lid formed on the base wall and at least one hook extending from the cover which is positioned to snap over and engage the lip on the base wall when the cover is moved to its closed position, wherein there are a plurality of lips and hooks and wherein one lip is formed on the forwardmost portion of the base wall and a corresponding hook is formed on a corresponding forwardmost portion of the cover to engage the forwardmost lip on the base wall, and further including lips extending from the base wall at positions near the hinge and hooks extending from the cover at positions near the hinge to engage the lips on the base wall near the hinge as the cover is moved to its closed position.

11. The protector of claim 5 wherein the base, hinge, and cover are integrally formed of plastic and the hinge is made of thin plastic to form a flexible hinge.

12. The protector of claim 6 wherein the base, hinge and cover are integrally formed of plastic and the hinge is made of thin plastic to form a flexible hinge, and wherein the cover includes a top wall and a back wall which extends downwardly from the top wall to the hinge whereby the back wall can engage the finger of the user to help prevent overflexing of the integral hinge.

13. A suture needle protector for holding a suture needle during a surgical operation, comprising:

(a) a base having an inner base surface on which a suture needle can be placed, a plate of permanent magnetic material forming at least part of the inner base surface whereby a surgical needle will be drawn to the magnetic plate and held thereon, and wherein the plate of magnetic material has spaced ribs formed therein such that a suture needle resting on top of the ribs may be readily removed from the protector by engaging the suture needle in the space between the ribs under the suture needle;

(b) a cover sized to close over the base to hold a suture needle on the inner base surface surrounded by the base and the cover;

(c) a hinge hingedly attaching the cover to the base so that the cover can be moved from a closed position in which the cover and base enclose a suture needle to an opened position in which a suture needle can be placed in or removed from the area of the inner base surface;

(d) a strap of flexible material having ends attached to the base so that a user can insert a finger between the base and the strap to hold the protector on the finger of the user; and (e) means for releasably holding the cover closed onto the base comprising at least one lip formed on the base wall and at least one hook extending from the cover which is positioned to snap over and engage the lip on the base wall when the cover is moved to its closed position, and wherein one of said at least one lip is formed on the forwardmost portion of the base wall and a corresponding one of said at least one hook is formed on a corresponding forwardmost portion of the cover to engage said forwardmost lip on the base wall, and further including lips extending from the base wall at positions near the hinge and hooks extending from the cover at positions near the hinge to engage the lips on the base wall near the hinge as the cover is moved to its closed position.

\* \* \* \* \*